United States Patent [19]

Suzuki et al.

[11] Patent Number: 4,916,067

[45] Date of Patent: Apr. 10, 1990

[54] METHOD FOR THE PREPARATION OF SORBIC ACID BY OXIDIZING 2,4-HEXADIENAL WITH A MICROORGANISM

[75] Inventors: Motoshi Suzuki; Nobuo Murakami; Akira Inoue, all of Sodegaura, Japan

[73] Assignee: Idemitsu Kosan Company Limited, Tokyo, Japan

[21] Appl. No.: 321,968

[22] Filed: Mar. 9, 1989

Related U.S. Application Data

[63] Continuation-in-part of Ser. No. 254,938, PCT JP87/00986 on Dec. 16, 1987, abandoned.

[30] Foreign Application Priority Data

Dec. 17, 1986 [JP] Japan ............................ 61-300425
Apr. 15, 1988 [JP] Japan ............................ 63-91736

[51] Int. Cl.$^4$ .................... C12P 7/40; C12R 1/01; C12R 1/40
[52] U.S. Cl. .................................. 435/136; 435/42; 435/252.34; 435/822; 435/840; 435/843
[58] Field of Search ............... 435/136, 252.34, 877, 435/822

[56] References Cited

FOREIGN PATENT DOCUMENTS 0289822 11/1988 European Pat. Off. ............ 435/136
0059131  5/1980 Japan ................................. 435/136
0113891  6/1984 Japan ................................. 435/136

OTHER PUBLICATIONS

Chem. Abs., vol. 100, #3, 1983, 21536c (Simon et al.), "Chiral Synthons by Biohydrogenation or Electro-Enz Red".

Primary Examiner—Herbert J. Lilling
Attorney, Agent, or Firm—Frishauf, Holtz, Goodman & Woodward

[57] ABSTRACT

Sorbic acid can be prepared by the activity of a specific microorganism on 2,4-hexadienal. This method can be performed under mild conditions and, different from organo-chemical methods, is advantageous because no by-products are formed.

8 Claims, No Drawings

METHOD FOR THE PREPARATION OF SORBIC ACID BY OXIDIZING 2,4-HEXADIENAL WITH A MICROORGANISM

This application is a Continuation-in-part of application Ser. No. 07/254,938 filed as PCT JP87/00986 on Dec. 16, 1987, now abandoned.

BACKGROUND OF THE INVENTION

The present invention relates to a method for the preparation of sorbic acid or, more particularly, relates to a method for the preparation of sorbic acid by the activity of a specific microorganism on 2,4-hexadienal.

The thus obtained sorbic acid can be utilized in the field of food industry as an antiseptic acd the like, and also is useful as a starting material of synthetic resins and others.

In the preparation of sorbic acid, formation of by-products is unavoidable when 2,4-hexadienal as the starting material is oxidized in a procedure of organic chemistry. Therefore, a procedure of purification is indispensable in order to obtain sorbic acid of high purity while the procedure is troublesome and sorbic acid having a desired purity can be obtained only with difficulty.

SUMMARY OF THE INVENTION

Accordingly, the present invention has an object to provide a method for the preparation of sorbic acid with high efficiency.

The inventors have conducted investigations to develop a method for the preparation of sorbic acid from 2,4-hexadienal by utilizing a microorganism and arrived at a discovery that sorbic acid of high purity can be prepared from 2,4-hexadienal by selecting and using a specific microorganism leading to completion of the present invention on the base of this discovery.

Thus, the present invention relates to a method which comprises bringing at least one kind of microorganisms having an activity to oxidize 2,4-hexadienal and belonging to either one of the genuses of Arthrobacter, Bacillus, Bacteridium, Brevibacterium, Citrobacter, Corynebacterium, Enterobacter, Escherichia, Flavobacterium, Klebsiella, Micrococcus, Microbacterium, Nocardia, Paracoccus, Proteus, Pseudomonas, Serratia, Rhodotorula and Saccharomycopsis.

DETAILED DESCRIPTION OF THE PREFERRED EMBODIMENTS

The microorganism utilizable in the present invention is a microorganism belonging to either one of the above named various genuses and should have an activity to oxide 2,4-hexadienal. Particular examples thereof include *Arthrobacter oxydans* IFO 12138, *Arthrobacter aurescens* IAM 12340, *Bacillus cereus* IFO 3131, *Bacteridium sp. R* 341 CBS 496.74, *Brevibacterium lactofermentum* ATCC 21420, *Brevibacterium flavum* ATCC 13826, *Brevibacterium roseum* ATCC 13825, *Brevibacterium ammoniagenes* ATCC 13746, *Corynebacterium glutamicum* ATCC 13032, *Corynebacterium herculis* ATCC 18868, *Corynebacterium sp.* ATCC 21341, *Enterobacter cloacae* IFO 3320, *Escherichia coli* ATCC 11303, ATCC 9723E and ATCC 9723D, *Flavobacterium suaveolens* IFO 3752, *Klebsiella pneumoniae* IFO 3318, *Micrococcus sp. A111* CBS 497.74, *Microbacterium ammoniaphilum* ATCC 15354, *Rhodococcus erythropolis* IFO 12320, *Nocardia sp.* ATCC 21145, *Paracoccus denitrificans* IFO 13301, *Proteus mirabilis* IFO 3849, *Pseudomonas pseudoalkaligenes* ATCC 12815, *Pseudomonas aeruginosa* ATCC 15524, *Pseudomonas acidovorans* ATCC 15688, *Pseudomonas putida* SI-21 (FERM BP-1800) *Serratia marcescens* IAM 1205, *Rhodotorula minuta* IFO 387, *Saccharomycopsis lipolytica* IFO 746, and the like. Then can be used either singly or as a combination of two kinds or more.

A microorganism capable of oxidizing 2,4-hexadienal is newly isolated from a soil by the inventors and named as *Pseudomonas putida* SI-21 having microbiological properties given below.

1. Growth condition on culture medium
(1) Plate culture: agar culture medium, Difco, pH 7.2, 28° C., after culturing for 48 hours
  Size of colonies: 1.5 to 3.0 mm×1.5 to 3.0 mm
  Form: circular
  Tubercle: convex disc
  Surface: smooth
  Form of periphery: entire
  Color: greyish white
  Illuminance: none
  Luster: bright
  Opacity: opaque
  Consistency: butter-like
  Emulsification: easy
  Suspension: uniform
(2) Slant culture: agar culture medium, Difco, pH 7.2, 28° C., after culturing for 48 hours
  Growing: good
  Surface: smooth or warty
  Color: greyish white
  Opacity: opaque
  Illuminance: none
  Luster: bright
(3) Liquid culture: bouillon culture medium, Difco, pH 7.2, 28° C., after culturing for 48 hours
  Surface: filmy
  Turbidity: strong
  Precipitates: dense
  Quantity: little
  Gas formation: none
  Odor: none
  Color: colorless
  Viscidity: none but yes after 4 days of culturing 2. Morphological and cytological properties: agar culture medium, Difco, pH 7.2, 28° C., after culturing for 24 hours
(1) Morphological properties
  Form: short rod-shaped
  Size: 1.0 to 1.4 μm×1.2 to 2.0 μm
  Arrangement: usually single but sometimes tandem or chains of 3 to 7
(2) Cytological properties
  Gram's stain: negative
  Acid fastness: negative
  Capsule: none
  Mobility: +
  Flagellum: polar flagellum
  Spore: not formed 3. Physiological properties: in culturing on agar culture medium, Difco
  Temperature of growth: 11° to 37° C.
  Optimum temperature: 25° to 33° C.
  pH of growth: 5 to 9.5
  Optimum pH: 6 to 8
  Anaerobic growth: −
  Growth in bouillon culture medium: good
  Growth in $NH_4$-N culture medium: good
  Growth in $NO_3$-N culture medium: good Growth in peptone water culture medium: good
Growth in 12% NaCl-bouillon culture medium: negative
Growth factor: non-requisite
$Na^+$: non-requisite
Catalase: +
Oxidase: +
O-F test: oxidative
Liquefaction of gelatin: −
Hydrolysis of starch: −
Decomposition of urea: −
Decarbonation of arginine: +
Litmus milk: alkaline
Formation of indole: −
VP test: −
MR test: −
Formation of hydrogen sulfide: −
Formation of ammonia: +
Utilization of carbohydrates, formation of acid and gas
 Xylose: −
 Arabitose: −
 Glucose: acid
 Ethanol: −
 Fructose: acid
 Mannose: acid
 Galactose: −
 Sucrose: acid
 Lactose: −
 Maltose: acid
 Trehalose: acid
 Mannitol: −
 Sorbitol: −
 Inositol: −
 Glycerin: acid
 Starch: −
Utilization of carbon sources
 Citrate Koser: +
 Citrate Christensen: +
 Citrate Simmons: +
Accumulation of poly-$\beta$-hydroxybutyrate: −
 Reduction of nitrates: −
 Denitrification activity: −
 Nitrogen fixation: −
Formation of coloring matter, on agar culture medium
 Pseudomonas F agar: water-soluble yellow coloring matter with fluorescence
 Pseudomonas P agar: none
Growth in nitrogen-free culture medium: −

The result of survey of the description in Manual of Determinative Bacteriology, 8th edition, by Barjey indicates that the above described bacteriological properties of the strain of SI-21 are very close to those of *Pseudomonas putida* so that the strain of SI-21 is given a name of *Pseudomonas putida* SI-21 according to the proposition of the inventors. The strain is deposited at and available from Agency of Industrial Science and Technology, Institute of Microbiological Industry under a deposition No. of FERM BP-1800.

In the method of the present invention, any bacterial strains obtained by artificial or spontaneous mutation can be used equally provided that the strain has an activity of producing sorbic acid by oxidizing 2,4-hexadienal.

The microorganisms can be used in a variety of forms. For example, any of the microbial cells in the periods of multiplication and dormancy as well as immobilized microbial cells can be used. Further, extracted materials from the cells of the microorganisms can be used. Immobilization of the microbial cells can be performed by a conventional method for immobilization such as the carrier-binding method, crosslinking method, entrapment method and the like. A method suitable as the method of extraction is that the microbial cells in a suspension are disintegrated by means of ultrasonic waves, French press, high-pressure homogenizer and the like followed by centrifugal separation and the like to give a soluble extracted material.

On the other hand, 2,4-hexadienal has a byname of sorbinaldehyde and can be converted into sorbic acid by the oxidation reaction using the above microorganisms.

The culture medium used for culturing the above microorganisms should contain carbon sources, nitrogen sources and the like to facilitate growth of the microorganisms. Various compounds can be used as the carbon source provided that the compound is not inhibitive of the activity of the microorganism for the production of sorbic acid including, for example, glucose, sucrose, ethyl alcohol, ethylene glycol, propylene glycol, 1,4-butane diol, glycerin, acetaldehyde, acetic acid, propionic acid and the like. Any nitrogen source material can be used provided that it is not inhibitive of the activity of the microorganism for the production of sorbic acid including meat extract, peptone,ccorn steep liquor, yeast extract, urea, ammonium salts such as ammonium sulfate, ammonium chloride, nitrates such as sodium nitrate and the like. Further, if necessary, the culture medium may be admixed with an appropriate amount of inorganic salts such as phosphates and salts of magnesium, calcium, iron, copper, zinc and the like and nutrients supporting growth of the microorganism.

2,4-Hexadienal is brought into contact with the microorganism in various ways. For example, it can be added at one time or added portionwise in several times to a medium containing the microorganisms. It is, however, preferable that 2,4-hexadienal is added in several portions or continuously at a controlled rate in order to keep a relatively low concentration of 2,4-hexadienal as the substrate in the medium. A preferable concentration of 2,4-hexadienal in the medium is in the range from 1 to 200 g per liter. The moment of addition thereof is also not limitative and the culture medium can be admixed therewith either prior to innoculation with the microorganisms or during or after culture of the microorganisms depending on the type of the microorganisms. Alternatively, it can be added to a suspension of the microbial cells collected from the cultured broth.

2,4-hexadienal in the presence of the above microorganisms should be oxidized under an aerobic condition determined in the properties of the microorganism to be used. The temperature, length of time, pH and the like in the reaction are not particularly limitative provided that sorbic acid as the desired product can be produced in a high purity and with a high efficiency. For example, the temperature should be from 5° to 80° C. or, preferably, 10° to 50° C. and the pH should be 3 to 10 or, preferably 5 to 8. When *Pseudomonas putida* SI-2(FERM BP-1800) is used, the reaction temperature is in the range from 5° to 60° C. or, preferably, from 10° to 35° C. and the pH of the reaction medium is in the range from 4 to 11 or, preferably, from 5.5 to 7.

The reaction can be performed in further different ways such as a combination of the culturing method using the microorganisms in the period of multiplication and the reaction with resting microbial cells, reaction by use of an extracted material from the microbial cells as such or as a combination with the above mentioned method, and so on.

After completion of the reaction, the sorbic acid as the desired product can be isolated and purified according to a conventional method after solid-liquid separation.

EXAMPLES

In the following, the present invention is described in detail by way of examples.

EXAMPLE 1

One loopfull of microbial cells of *Rhodococcus erythropolis* IFO 12320 was innoculated to 100 ml of culture medium (Table 1) in a Sakaguchi flask and shaking culture was performed at 30° C. for 48 hours. After cultivation, the cultured broth was subjected to centrifugal separation at 5° C. for 10 minutes under 11,000 G and the thus obtained harvested cells were washed with a 1/15M phosphate buffer solution(pH 7) and then suspended in 10 ml of a 1/15M phosphate buffer solution to OD10. 10 mM of 2,4-hexadienal was admixed to the suspension and was oxidized at 30° C. for 30 minutes.

After oxidation, a portion of the reaction mixture was taken and subjected to centrifugal separation to remove the microbial cells. The supernatant was then acidified with a 6N hydrochloric acid to have a pH of 2 and subjected to quantitative analysis by gas chromatography to find that sorbic acid was formed in a yield of 56 mg/liter. The gas chromatography was performed by using a column filled with Thermon 3000 on celite 545 as the stationary phase and kept at a temperature of 160° C. with a nitrogen flow rate of 50 ml/minute. The retention time of sorbic acid under these conditions was 4 times.

TABLE 1

| Meat extract | 5.0 g |
|---|---|
| Peptone | 15.0 g |
| Ammonium chloride | 5.0 g |
| $KH_2PO_4$ | 5.0 g |
| 1,4-Butane diol | 5.0 g |

*diluted to 1 liter with distilled water (pH 7.0)

EXAMPLE 2

Reactions were undertaken each in the same manner as in Example 1 excepting the use of the strains of the microorganisms indicated in Table 2 in place of the microorganisms in Example 1. The results are shown in Table 2.

TABLE 2

| Microbial strain | Yield of sorbic acid, mg/liter |
|---|---|
| *Arthrobacter oxydans* IFO 12138 | 20 |
| *Arthrobacter aurescens* IAM 12340 | 52 |
| *Bacillus cereus* IFO 3131 | 79 |
| *Bacteridium sp.* R 341 CBS 496.74 | 34 |
| *Brevibacterium lactofermentum* ATCC 21420 | 82 |
| *Brevibacterium flavum* ATCC 13826 | 229 |
| *Brevibacterium roseum* ATCC 13825 | 154 |
| *Brevibacterium ammoniagenes* ATCC 13746 | 156 |
| *Corynebacterium sp.* ATCC 21341 | 38 |
| *Corynebacterium glutamicum* ATCC 13032 | 191 |
| *Corynebacterium herculis* ATCC 13868 | 74 |
| *Enterobacter cloacae* IFO 3320 | 25 |
| *Escherichia coli* ATCC 11303 | 32 |
| *Escherichia coli* ATCC 9723E | 38 |
| *Escherichia coli* ATCC 9723D | 67 |
| *Flavobacterium suaveolens* IFO 3752 | 35 |
| *Klebsiella pneumonia* IFO 3318 | 36 |

TABLE 2-continued

| Microbial strain | Yield of sorbic acid, mg/liter |
|---|---|
| *Micrococcus sp.* AIII CBS 497.74 | 22 |
| *Microbacterium ammoniaphilum* ATCC 15354 | 37 |
| *Nocardia sp.* ATCC 21145 | 25 |
| *Paracoccus denitrificans* IFO 13301 | 40 |
| *Proteus mirabilis* IFO 3849 | 418 |
| *Pseudomonas pseudoalkaligenes* ATCC 12815 | 597 |
| *Pseudomonas acidovorans* ATCC 15668 | 194 |
| *Pseudomonas aeruginosa* ATCC 15524 | 445 |
| *Serratia marcescens* IAM 1205 | 54 |
| *Rhodotorula minuta* IFO 387 | 95 |
| *Saccharomycopsis lipolytica* IFO 746 | 126 |

EXAMPLE 3

The strain of *Pseudomonas putida* SI-21 (FERM BP-1800) was inoculated to 10 ml of a culture medium having a pH of 7 and containing 5 g/liter of 1,4-butane diol, 2 g/liter of ammonium sulfate $(NH_4)_2SO_4$, 1.5 g/liter of potassium dihydrogen phosphate $KH_2PO_4$, 1.5 g/liter of disodium hydrogen phosphate dodecahydrate $Na_2HPO_4.12H_2O$, 0.2 g/liter of magnesium sulfate heptahydrate $MgSO_4.7H_2O$, 0.01 g/liter of calcium chloride dihydrate $CaCl_2.2H_2O$, 0.01 g/liter of iron (II) sulfate heptahydrate $FeSo_4.7H_2O$. 0.05 g/liter of corn steep liquor and 0.05 g/liter of yeast extract and culturing of the microorganism was performed at 30° C. for 48 hours. After cultivation, the cultured broth was subjected to centrifugal separation and the thus obtained harvested cells were washed with a 1/15M phosphate buffer solution (pH 7) and then suspended in 10 ml of a 1/15M phosphate buffer solution. 1 µl of 2,4-hexadienal was admixed to the suspension and was oxidized at 30° C. for 15 minutes.

After oxidation, the reaction mixture was acidified with a drop of 1N hydrochloric acid and was subjected to centrifugal separation to remove the microbial cells. The supernatent was subjected to quantitative analysis by gas chromatography to find that sorbic acid was formed in a yield of 1.1 g/liter.

EXAMPLE 4

Bacterial cells of *Pseudomonas putida* SI-21 (FERM BP1800) obtained in the same manner as in Example 3 were suspended in 1 ml of a 1/15 M phosphate buffer solution containing 30 g/liter of sorbic acid, to which 1 µl of 2,4-hexadienal was added to effect the reaction at 30° C. for 15 minutes. After the reaction, a drop of 1N hydrochloric acid was added to the reaction mixture which was subjected to centrifugation to remove the cells. The result of the gas chromatographic analysis of the supernatent indicated complete disappearance of 2,4-hexadienal therein. This fact supports the conclusion that sorbic acid as the reaction product of the reaction has no inhibitive effect on the reaction per se.

INDUSTRIAL UTILIZABILITY

Sorbic acid can be prepared with high efficiency from 2,4-hexadienal by specific microorganisms according to the present invention. Different from conventional procedures of organic chemistry, in particular, the reaction proceeds quantitatively and no by-products are formed so that sorbic acid of high purity can be obtained under mild conditions. The thus obtained sorbic acid can be utilized in the field of food industry as an antiseptic and the like and, in addition, it is useful as a starting material of synthetic resins and so on.

We claim:

1. A method for the preparation of sorbic acid which comprises oxidizing 2,4-hexadienal by bringing at least one kind of microorganisms having an activity to oxidize 2,4-hexadienal and belonging to either one of the genuses of Arthrobacter, Bacillus, Bacteridium, Brevibacterium, Citrobacter, Corynebacterium, Enterobacter, Escherichia, Flavobacterium, Klebsiella, Micrococcus, Microbacterium, Nocardia, Rhodococcus, Paracoccus, Proteus, Pseudomonas, Serratia, Rhodotorula and Saccharomycopsis into contact with the 2,4-hexadienal.

2. The method according to claim 1 wherein the microorganism is in the form selected from the group consisting of microbial cells in the period of multiplication, resting microbial cells, immobilized microbial cells and extracted materials from the microbial cells.

3. A method of oxidizing 2,4-hexadienal to sorbic acid of high purity which comprises bringing a microorganism, or an extract thereof, which displays activity to oxidize 2,4-hexadienal, and which is selected from the genuses consisting of Arthrobacter, Bacillus, Bacteridium Brevibacterium, Citrobacter, Corynebacterium, Enterobacter, Escherichia, Flavobacterium, Klebsiella, Micrococcus, Microbacterium, Nocardia, Rhodococcus, Paracoccus, Proteus, Pseudomonas, Serratia, Rhodotorula and Saccharomycopsis into contact with the 2,4-hexadienal.

4. The method of claim 3 wherein the 2,4-hexadienal is oxidized at a temperature of 5° to 80° C. and at a pH of 3 to 10.

5. The method of claim 4 wherein the temperature is 10° to 50° C. and the pH is 5 to 8.

6. A method of oxidizing 2,4-hexadienal to sorbic acid of high purity comprising a microorganism, or an extract thereof, which displays activity to oxidize 2,4-hexadienal, and which is selected from the group consisting of

*Rhodococcus erythropolis* IFO 12320
*Arthrobacter oxydans* IFO 12138
*Arthrobacter aurescens* IAM 12340
*Bacillus cereus* IFO 3131
*Bacterium sp.* R 341 CBS 496.74
*Brevibacterium lactofermentum* ATCC 21420
*Brevibacterium flavum* ATCC 13826
*Brevibacterium roseum* ATCC 13825
*Brevibacterium ammoniagenes* ATCC 13746
*Corynebacterium sp.* ATCC 21341
*Corynebacterium qlutamicum* ATCC 13032
*Corynebacterium herculis* ATCC 13868
*Enterobacter cloacae* IFO 3320
*Escherichia coli* ATCC 11303
*Escherichia coli* ATCC 9723E
*Escherichia coli* ATCC 9723D
*Flavocacterium suaveolens* IFO 3752
*Klebsiella pneumonia* IFO 3318
*Micrococcus sp. Alll* CBS 497.74
*Microbacterium ammoniaphilum* ATCC 15354
*Nocardia sp.* ATCC 21145
*Paracoccus denitrificans* IFO 13301
*Proteus mirabilis* IFO 3849
*Pseudomonas putida* SI-21 (FERM BP-1800)
*Pseudomonas pseudoalkaligenes* ATCC 12815
*Pseudomonas acidovorans* ATCC 15668
*Pseudomonas aeruginosa* ATCC 15524
*Serratia marcescens* IAM 1205
*Rhodotorula minuta* IFO 387 and
*Saccharomycopsis lipolytica* IFO 746.

7. The method of claim 6 wherein the 2,4-hexadienal is oxidized at a temperature of 5° to 80° C. and at a pH of 3 to 10.

8. The method of claim 7 wherein the temperature is 10° to 50° C. and the pH is 5 to 8.

* * * * *